(12) United States Patent
Rowland

(10) Patent No.: US 7,541,319 B2
(45) Date of Patent: Jun. 2, 2009

(54) 1,3-DITHIOLANE-2-THIONE ADDITIVES FOR LUBRICANTS AND FUELS

(75) Inventor: Robert G. Rowland, Woodbridge, CT (US)

(73) Assignee: Chemtura Corporation, Middlebury, CT (US)

(*) Notice: Subject to any disclaimer, the term of this patent is extended or adjusted under 35 U.S.C. 154(b) by 498 days.

(21) Appl. No.: 11/168,702

(22) Filed: Jun. 27, 2005

(65) Prior Publication Data

US 2006/0089273 A1 Apr. 27, 2006

Related U.S. Application Data

(60) Provisional application No. 60/621,670, filed on Oct. 26, 2004.

(51) Int. Cl.
C10M 135/34 (2006.01)
C07D 327/04 (2006.01)
C07D 343/00 (2006.01)

(52) U.S. Cl. .......... 508/300; 508/302; 549/30; 549/62

(58) Field of Classification Search .......... 508/284, 508/299, 300, 302; 549/30, 62
See application file for complete search history.

(56) References Cited

U.S. PATENT DOCUMENTS

| | | | | |
|---|---|---|---|---|
| 2,440,991 A | 5/1948 | Wayo | ............ | 252/48.6 |
| 2,498,936 A | 2/1950 | Badertscher et al. | ........ | 260/455 |
| 3,166,580 A | 1/1965 | Stanley et al. | ............ | 260/455 |
| 3,293,181 A | 12/1966 | Stuart | ............ | 252/32.7 |
| 3,396,109 A | 8/1968 | Butler et al. | ............ | 252/32.7 |
| 3,397,145 A | 8/1968 | Cyba | ............ | 252/32.7 |
| 3,442,804 A | 5/1969 | Suer et al. | ............ | 252/32.7 |
| 3,445,480 A | 5/1969 | Allais et al. | | |
| 3,481,871 A | 12/1969 | Myers et al. | ............ | 252/45 |
| 3,637,499 A | 1/1972 | Pollak | ............ | 252/32.7 |
| 3,637,749 A * | 1/1972 | O'Connor | ............ | 549/39 |
| 3,818,041 A * | 6/1974 | Fields | ............ | 549/33 |
| 4,072,692 A | 2/1978 | Daum | | |
| 4,240,821 A * | 12/1980 | Rasheed et al. | ............ | 504/290 |
| 4,511,464 A * | 4/1985 | Bergman | ............ | 209/166 |
| 4,605,519 A * | 8/1986 | Bergman | ............ | 558/234 |
| 4,618,461 A * | 10/1986 | Bergman et al. | ............ | 558/234 |
| 4,908,142 A | 3/1990 | Dumdum et al. | ............ | 252/17 |
| 5,084,195 A | 1/1992 | Camenzind et al. | ........ | 252/47.5 |
| 5,300,243 A | 4/1994 | Camenzind et al. | ........ | 252/47.5 |
| 5,498,809 A | 3/1996 | Emert et al. | ............ | 585/13 |
| 5,512,190 A | 4/1996 | Anderson et al. | ............ | 252/47 |
| 5,514,189 A | 5/1996 | Farng et al. | ............ | 44/383 |
| 5,834,407 A * | 11/1998 | Manka et al. | ............ | 508/271 |
| 6,255,260 B1 * | 7/2001 | Stork | ............ | 508/421 |
| 6,551,966 B2 | 4/2003 | Nalesnik | ............ | 508/277 |
| 2004/0060229 A1 * | 4/2004 | Todd et al. | ............ | 44/603 |

FOREIGN PATENT DOCUMENTS

| | | |
|---|---|---|
| EP | 0825246 A2 | 2/1998 |
| JP | 4637176 | 11/1971 |
| JP | 46037176 | 11/1971 |
| JP | 63218672 | 9/1988 |
| SU | 1082784 | 3/1984 |
| SU | 1268573 | 11/1986 |
| SU | 1351924 | 11/1987 |
| SU | 1361142 | 12/1987 |
| SU | 1425191 | 9/1988 |
| SU | 1439098 | 11/1988 |
| SU | 1447818 | 12/1988 |

OTHER PUBLICATIONS

Barbero et al., "Convenient Procedure for Converting 1,3-Dithiolane-2-Thiones into 1,3-Dithiolan-2-Ones" appearing in Journal of the Chemical Society, Perkin Transactions 1, Chemical Society. No. 3, pp. 289-294 (1996).

Ali et al., Conversion of Aliphatic and Alicyclic Epoxides into Trithiocarbonates, JCS Perkin I, 1975, pp. 748-755.

* cited by examiner

Primary Examiner—Glenn Caldarola
Assistant Examiner—Jim Goloboy
(74) Attorney, Agent, or Firm—Jaimes Sher

(57) ABSTRACT

Fuels, especially hydrocarbon fuels, and lubricants, especially lubricating oils, contain a class of anti-corrosion, anti-wear, anti-fatigue, and extreme pressure additives that are derived from 1,3-dithiolane-2-thiones.

13 Claims, No Drawings

1,3-DITHIOLANE-2-THIONE ADDITIVES FOR LUBRICANTS AND FUELS

I claim the benefit under Title 35, United States Code, §120 of U.S. Provisional Application No. 60/621,670, filed Oct. 26, 2004, entitled 1,3DITHIOLANE-2-THIONE ADDITIVES FOR LUBRICANTS AND FUELS.

BACKGROUND OF THE INVENTION

1. Field of the Invention

The present invention is related to fuels, especially hydrocarbon fuels, and lubricants, especially lubricating oils, and, more particularly, to a class of anti-corrosion, anti-wear, anti-fatigue, and extreme pressure additives that are derived from 1,3-dithiolane-2-thiones (cyclic trithiocarbonates) for such fuels and lubricants.

2. Description of Related Art

In developing lubricating oils, there have been many attempts to provide additives that impart anti-fatigue, anti-wear, and extreme pressure properties thereto. Zinc dialkyldithiophosphates (ZDDP) have been used in formulated oils as anti-wear additives for more than 50 years. However, zinc dialkyldithiophosphates give rise to ash, which contributes to particulate matter in automotive exhaust emissions, and regulatory agencies are seeking to reduce emissions of zinc into the environment. In addition, phosphorus, also a component of ZDDP, is suspected of limiting the service life of the catalytic converters that are used on cars to reduce pollution. It is important to limit the particulate matter and pollution formed during engine use for toxicological and environmental reasons, but it is also important to maintain undiminished the anti-wear properties of the lubricating oil.

In view of the aforementioned shortcomings of the known zinc and phosphorus-containing additives, efforts have been made to provide lubricating oil additives that contain neither zinc nor phosphorus or, at least, contain them in substantially reduced amounts. Illustrative of non-zinc, i.e., ashless, non-phosphorus-containing lubricating oil additives are the reaction products of 2,5-dimercapto-1,3,4-thiadiazoles and unsaturated mono-, di-, and tri-glycerides disclosed in U.S. Pat. No. 5,512,190 and the dialkyl dithiocarbamate-derived organic ethers of U.S. Pat. No. 5,514,189.

U.S. Pat. No. 5,512,190 discloses an additive that provides anti-wear properties to a lubricating oil. The additive is the reaction product of 2,5-dimercapto-1,3,4-thiadiazole and a mixture of unsaturated mono-, di-, and triglycerides. Also disclosed is a lubricating oil additive with anti-wear properties produced by reacting a mixture of unsaturated mono-, di-, and triglycerides with diethanolamine to provide an intermediate reaction product and reacting the intermediate reaction product with 2,5-dimercapto-1,3,4 thiadiazole.

U.S. Pat. No. 5,514,189 discloses that dialkyl dithiocarbamate-derived organic ethers have been found to be effective anti-wear/antioxidant additives for lubricants and fuels.

U.S. Pat. No. 2,440,991 discloses the use of acyclic trithiocarbonates that are S,S' disubstituted with carboxylic acids of 16 to 18 carbons. These compounds are said to be useful as rust inhibitors for lubricants.

U.S. Pat. No. 2,498,936 discloses the use of acyclic trithiocarbonates as extreme pressure additives. These additives are prepared by the reaction of the salts of a trithiocarbonate with an alkyl dihalide. The use of alkyl halides in the preparation of lubricant additives is now environmentally undesirable, as this may tend to increase the levels of halogen present in the finished additive.

U.S. Pat. No. 3,166,580 discloses the preparation of dicyclopentyltrithiocarbonate from alkali metal trithiocarbonates and cyclopentyl halides, and the use of the resulting product as "lubricating additives".

U.S. Pat. No. 3,481,871 discloses organo-sulfur derivatives that are produced by reacting a mercaptan with a sulfur chloride compound, reacting the resulting organic organic sulfenyl or thiosulfenyl chloride with and olefin, and finally reacting the resulting product with a metal sulfur-containing salt. The final product may be used in lubricating oils and other industrial fluids as a load-carrying additive.

U.S. Pat. No. 4,908,142 discloses additives containing a salt or complex of trithiocarbonic acid that are said to be useful in lubricants to enhance the extreme pressure/anti-wear and anti-oxidation capabilities thereof. The lubricants are preferably oils of lubricating viscosity, which may be thickened to a grease-like consistency with one or more oil thickeners, and contain from about 0.1 to about 20 weight percent of said additives.

U.S. Pat. Nos. 5,084,195 and 5,300,243 disclose N-acyl-thiourethane thioureas as anti-wear additives specified for lubricants or hydraulic fluids.

U.S. Pat. No. 6,551,966 discloses a composition comprising:
(A) a lubricant, and
(B) at least one 5-alkyl-2-mercapto-1,3,4-oxadiazole compound of the formula:

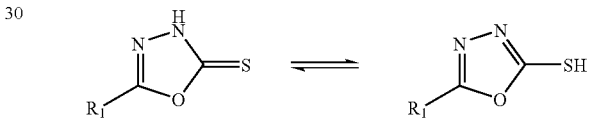

wherein $R_1$ is a hydrocarbon or functionalized hydrocarbon of from 1 to 30 carbon atoms.

Soviet Patent Nos. SU 1,447,818; SU 1,439,098; SU 1,425,191; SU 1,361,142; SU 1,351,924; SU 1,268,573; and SU 1,082,784 describe the use of acyclic S-alkyl, S-alkyl' disubstituted trithiocarbonates as multifunctional additives for lubricants, particularly anti-scuffing agents.

JP 46,037,176 discloses the use of the unsubstituted compound 1,3-dithiolane-2-thione as a non-corrosive extreme pressure agent for lubricants.

The disclosures of the foregoing are incorporated herein by reference in their entirety.

SUMMARY OF THE INVENTION

It has now been found that substituted 1,3-dithiolane-2-thiones, which are trithiocarbonates contained within a five membered ring, are useful as lubricant additives, imparting anti-wear and anti-corrosive properties to the lubricant. The presence of properly chosen substituents can impart improved solubility of the additive in the lubricant. These substituted 1,3-dithiolane-2-thiones can be conveniently prepared by reaction of an alkali metal xanthate with an appropriate oxirane (epoxide), and can be used either alone or in synergistic combination with a zinc dihydrocarbyldithiophosphate or an ashless phosphorus-containing additive, such as trilauryl phosphate or triphenyl phosphate.

The present invention is directed to additives that can be used as either partial or complete replacements for the zinc dialkyldithiophosphates currently used. They can also be used in combination with other additives typically found in motor oils, as well as other ashless anti-wear additives. The typical additives found in motor oils include dispersants, detergents, anti-wear agents, extreme pressure agents, rust inhibitors, antioxidants, antifoamants, friction modifiers, Viscosity Index (V.I.) improvers, metal passivators, and pour point depressants.

The compounds employed in the practice of the present invention are substituted 1,3-dithiolane-2-thiones that are useful as non-phosphorus-containing, anti-corrosion, anti-fatigue, anti-wear, extreme pressure additives for fuels and lubricating oils.

The present invention also relates to lubricating oil compositions comprising a lubricating oil and a functional property-improving amount of at least one substituted 1,3-dithiolane-2-thione.

It is an object of the present invention to provide a new application for substituted 1,3-dithiolane-2-thiones, useful either alone or in combination with other lubricant additives.

The additives of the present invention are especially useful as components in many different lubricating oil compositions. The additives can be included in a variety of oils with lubricating viscosity including natural and synthetic lubricating oils and mixtures thereof. The additives can be included in crankcase lubricating oils for spark-ignited and compression-ignited internal combustion engines. The compositions can also be used in gas engine lubricants, turbine lubricants, automatic transmission fluids, gear lubricants, compressor lubricants, metal-working lubricants, hydraulic fluids, and other lubricating oil and grease compositions.

The class of anti-fatigue, anti-wear, and extreme pressure additives is 1,3-dithiolane-2-thiones has the following generic formula (I):

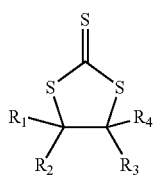

(I)

wherein:
$R_1$ is selected from the group consisting of hydrogen, alkyl, alkoxy, and carboxy alkyl of the structure:

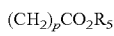

wherein:
p is from 1 to 50, and
$R_5$ is selected from the group consisting of hydrocarbyl, chain-substituted saturated hydrocarbyl, and chain-substituted unsaturated hydrocarbyl;

$R_2$, $R_3$, and $R_4$ are independently selected from the group consisting of hydrogen, alkyl, and alkenyl;
wherein said alkyl and alkenyl groups are unsubstituted or substituted with OH, SH, oxirane, thiirane, or 1,3-dithiolane-2-thione; or $R_1$ and $R_3$ are fused together to form a ring of from 3 to 10 carbon atoms, preferably 5 or 6 carbon atoms, which can be further substituted with alkyl, cycloalkyl, alkenyl, aryl, or alkoxy groups, and can contain ether or ester functionalities.

As employed herein, the term "hydrocarbyl" includes hydrocarbon as well as substantially hydrocarbon groups. "Substantially hydrocarbon" describes groups that contain heteroatom substituents that do not alter the predominantly hydrocarbon nature of the group. Examples of hydrocarbyl groups include the following:

(A) hydrocarbon substituents, i.e., aliphatic (e.g., alkyl or alkenyl), alicyclic (e.g., cycloalkyl, cycloalkenyl) substituents, aromatic substituents, aromatic-, aliphatic-, and alicyclic-substituted aromatic substituents, and the like, as well as cyclic substituents wherein the ring is completed through another portion of the molecule (that is, for example, any two indicated substituents may together form an alicyclic radical);

(B) substituted hydrocarbon substituents, i.e., those substituents containing non-hydrocarbon groups which, in the context of this invention, do not alter the predominantly hydrocarbon nature of the substituent; those skilled in the art will be aware of such groups (e.g., halo, hydroxy, mercapto, nitro, nitroso, sulfoxy, etc.);

(C) heteroatom substituents, i.e., substituents that will, while having a predominantly hydrocarbon character within the context of this invention, contain an atom other than carbon present in a ring or chain otherwise composed of carbon atoms (e.g., alkoxy or alkylthio). Suitable heteroatoms will be apparent to those of ordinary skill in the art and include, for example, sulfur, oxygen, nitrogen, and such substituents as, e.g., pyridyl, furyl, thienyl, imidazolyl, etc. Preferably, no more than about 2, more preferably no more than one, hetero substituent will be present for every ten carbon atoms in the hydrocarbyl group. More preferably, there will be no such heteroatom substituents in the hydrocarbyl group, i.e., the hydrocarbyl group is purely hydrocarbon.

More particularly, the present invention is directed to a composition comprising:
(A) a lubricant or a hydrocarbon fuel, and
(B) at least one 1,3-dithiolane-2-thione of formula (I):

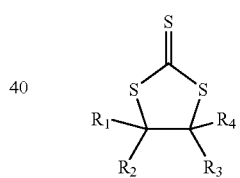

(I)

wherein:
$R_1$ is selected from the group consisting of hydrogen, alkyl, alkoxy, and carboxy alkyl of the structure:

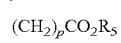

wherein:
p is from 1 to 50, and
$R_5$ is selected from the group consisting of hydrocarbyl, chain-substituted saturated hydrocarbyl, and chain-substituted unsaturated hydrocarbyl;

$R_2$, $R_3$, and $R_4$ are independently selected from the group consisting of hydrogen, alkyl, and alkenyl;
wherein said alkyl and alkenyl groups are unsubstituted or substituted with OH, SH, oxirane, thiirane, or 1,3-dithiolane-2-thione; or $R_1$ and $R_3$ are fused together to form a ring of from 3 to 10 carbon atoms, which can be further substituted with alkyl, cycloalkyl, alkenyl, aryl or alkoxy groups, and can contain ether or ester functionalities, and, optionally,
(C) at least one phosphorus-containing additive.

In another embodiment, the present invention is directed to a method for improving the anti-corrosion, anti-fatigue, antiwear, and extreme pressure properties of lubricants and hydrocarbon fuels comprising adding to said lubricants and hydrocarbon fuels a functional property-improving amount of at least one at least one 1,3-dithiolane-2-thione of formula (I):

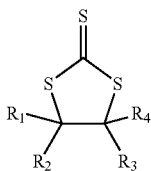

wherein:

R$_1$ is selected from the group consisting of hydrogen, alkyl, alkoxy, and carboxy alkyl of the structure:

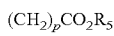

wherein:

p is from 1 to 50, and

R$_5$ is selected from the group consisting of hydrocarbyl, chain-substituted saturated hydrocarbyl, and chain-substituted unsaturated hydrocarbyl;

R$_2$, R$_3$, and R$_4$ are independently selected from the group consisting of hydrogen, alkyl, and alkenyl;

wherein said alkyl and alkenyl groups are unsubstituted or substituted with OH, SH, oxirane, thiirane, or 1,3-dithiolane-2-thione;

or

R$_1$ and R$_3$ are fused together to form a ring of from 3 to 10 carbon atoms, which can be further substituted with alkyl, cycloalkyl, alkenyl, aryl or alkoxy groups, and can contain ether or ester functionalities.

The 1,3-dithiolane-2-thione is present in the compositions of the present invention in a concentration in the range of from about 0.01 to about 10 wt %.

DESCRIPTION OF THE PREFERRED EMBODIMENTS

As stated above, the class of anti-fatigue, anti-wear, and extreme pressure additives can have the following formula (I):

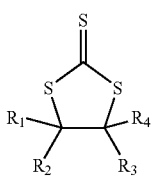

wherein:

R$_1$ is selected from the group consisting of hydrogen, alkyl, alkoxy, and carboxy alkyl of the structure:

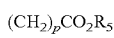

wherein:

p is from 1 to 50, and

R$_5$ is selected from the group consisting of hydrocarbyl, chain-substituted saturated hydrocarbyl, and chain-substituted unsaturated hydrocarbyl;

R$_2$, R$_3$, and R$_4$ are independently selected from the group consisting of hydrogen, alkyl, and alkenyl;

wherein said alkyl and alkenyl groups are unsubstituted or substituted with OH, SH, oxirane, thiirane, or 1,3-dithiolane-2-thione; or R$_1$ and R$_3$ are fused together to form a ring of from 3 to 10 carbon atoms, preferably 5 or 6 carbon atoms, which can be further substituted with alkyl, cycloalkyl, alkenyl, aryl or alkoxy groups, and can contain ether or ester functionalities.

Preferably, R$_1$ and R$_2$ are independently selected from the group consisting of:

(A) Alkyl groups of from 1 to 50 carbon atoms, including, but not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, triacontyl, isomers of the foregoing, and the like. By "isomers" such moieties as branched alkyls and cycloalkyls are intended to be included. Examples of such branched alkyls include isopropyl, isobutyl, isopentyl, isoheptyl, isooctyl, sec-butyl, 1-methylbutyl, 1-ethylpropyl, and the like. Examples of such cycloalkyls include cyclopropyl, cyclobutyl, cyclopentyl, cyclohexyl, cyclooctyl, and the like.

(B) Aryl groups of from 6 to 14 carbon atoms, preferably from 6 to 10 carbon atoms, such as phenyl and naphthyl.

(C) Alkaryl, alkoxyaryl, or alkoxyalkyl groups of from 1 to 50 carbon atoms, preferably from 2 to 12 carbon atoms, such as tolyl, xylyl, benzyl, methoxyphenyl, methoxymethyl, methoxyethyl, ethoxymethyl, ethoxyethyl, and the like.

In the formula described above, R$_5$ is preferably hydrocarbyl. Examples of R5 include, but are not limited to, straight chain or branched chain alkyl or alkenyl groups containing from one to fifty carbon atoms, including, but not limited to, methyl, ethyl, propyl, butyl, pentyl, hexyl, heptyl, octyl, 2-ethyl hexyl, nonyl, decyl, undecyl, dodecyl, tridecyl, tetradecyl, pentadecyl, hexadecyl, heptadecyl, octadecyl, oleyl, nonadecyl, eicosyl, heneicosyl, docosyl, tricosyl, tetracosyl, pentacosyl, triacontyl, isomers of the foregoing, and the like; and cycloalkyl groups, such as cyclopentyl, cyclohexyl, cycloheptyl, cyclooctyl, and cyclododecyl.

R$_5$ can also be:

(A) unsubstituted phenyl;

(B) phenyl substituted with one or more alkyl groups, such as methyl, ethyl, propyl, butyl, pentyl, hexyl, heptyl, octyl, nonyl, decyl, isomers of the foregoing, and the like;

(C) phenyl substituted with one or more alkoxy groups, such as methoxy, ethoxy, propoxy, butoxy, pentoxy, hexoxy, heptoxy, octoxy, nonoxy, decoxy, isomers of the foregoing, and the like;

(D) phenyl substituted with one or more alkyl amino or aryl amino groups; and (E) naphthyl and alkyl substituted naphthyl.

Even more preferably, R$_1$ is selected from the group consisting of hexyl, heptyl, octyl, nonyl, decyl, undecyl, dodecyl, tridecyl, tetradecyl, pentadecyl, hexadecyl, heptadecyl, and octadecyl, and R$_2$, R$_3$, and R$_4$ are hydrogen, or R$_1$ and R$_3$ are fused as cyclopentyl or cyclohexyl, or R$_1$ and R$_3$ are residues derived from an epoxidized fatty acid ester.

Most preferably, R$_1$ and R$_3$ are residues derived from an epoxidized 2-ethyl hexyl tallate ester; or R$_1$ is octyl, nonyl, decyl, undecyl, or dodecyl, and R$_2$, R$_3$, and R$_4$ are hydrogen.

Especially preferred substituted cyclic 1,3-dithiolane-2- thione additives for use in the practice of the present invention include those having the following structures:

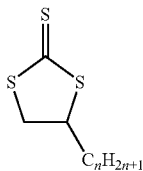

wherein n is an integer of from 1 to about 36, more preferably from 1 to about 18, most preferably from 8 to 12;

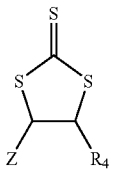

wherein Z is $(CH_2)_pCO_2R_3$ and the group $ZCHCHR_4$ is a residue from the reaction of a xanthate with an epoxidized unsaturated acid ester, such as an epoxidized ester of oleic, linoleic, linolenic, or eleostearic acid; or an epoxidized tall oil (tallate) ester, tallate and oleate esters being a preferred embodiment, and reaction products of 2-ethylhexyl tallate being particularly preferred;

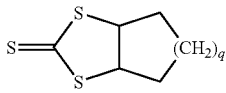

where q is 1 or 2.

The preparation of 1,3-dithiolane-2-thiones from epoxides is described and discussed by Owen, L. N. et al. in *J.C.S. Perkin Trans. I*, (8) 1975, 748-754, which is incorporated by reference herein.

A class of desirable, oil soluble 1,3-dithiolane-2-thione additives can be prepared by the reaction of an alkali metal xanthate, such as sodium butyl xanthate with an epoxidized α-olefin, such as epoxy dodecane or epoxy tetradecane, or mixtures thereof. These compounds are articles of commerce, available under the Vikolox® trademark from Arkema.

A particularly desirable, liquid, oil soluble 1,3-dithiolane-2-thione additive can be prepared by the reaction of a sodium xanthate with epoxidized 2-ethylhexyl tallate, which is an article of commerce available as Drapex® 4.4 from Crompton Corporation.

Suitable epoxides for use in the preparation of the 1,3-dithiolane-2-thiones employed in the practice of the present invention include propylene oxide, 1,2-epoxybutane, 1,2-epoxypentane, 1,2-epoxyheptane, 1,2-epoxyoctane, 1,2-epoxynonane, 1,2-epoxydecane, 1,2-epoxyundecane, 1,2-epoxydodecane, 1,2-epoxytetradecane, 1,2-epoxyhexadecane, 1,2-epoxyoctadecane, 1,2-epoxyeicosane, cyclohexene oxide, styrene oxide, phenyl propylene oxide, 4-nonylphenyl glicydal ether, butyl glycidal ether, 2-ethylhexyl glycidal ether, $C_8$-$C_{18}$ alkyl glycidal ethers, glycidal hexadecyl ether, o-cresyl glycidal ether, p-tert.-butyl phenyl glycidal ether, 1,2-epoxy-2-phenoxy propane, furfuryl glycidal ether, glycidal 4-methoxyphenyl ether, glycidal 2-methylphenyl ether, epoxidized $C_1$-$C_{18}$ esters of unsaturated $C_3$-$C_{36}$ carboxylic acids, particularly epoxidized esters of $C_{12}$-$C_{20}$ acids, such as epoxidized methyl tallate, epoxidized butyl tallate, epoxidized 2-ethylhexyl tallate, epoxidized octyl tallate, and epoxidized methyl oleate, epoxidized butyl oleate, epoxidized 2-ethylhexyl oleate, epoxidized octyl oleate, and the like; epoxidized unsaturated oils, such as epoxidized soybean oil, epoxidized canola oil, and the like.

The use of the 1,3-dithiolane-2-thiones of this invention can improve the anti-corrosion, anti-fatigue, anti-wear, and extreme pressure properties of a lubricant.

The substituted 1,3-dithiolane-2-thione additives of this invention can be used as either a partial or complete replacement for the zinc dialkyldithiophosphates currently used. The 1,3-dithiolane-2-thiones can be used either alone or in synergistic combination with (1) zinc dihydrocarbyldithiophosphates or (2) ashless phosphorus-containing additives or (3) mixtures of (1) and (2), in order to reduce the amounts of zinc and phosphorus that are currently used, without diminishing anti-wear performance. They can also be used in combination with other additives typically found in lubricating oils, as well as with other antiwear additives. The additives typically found in lubricating oils are, for example, dispersants, detergents, corrosion/rust inhibitors, antioxidants, anti-wear agents, anti-foamants, friction modifiers, seal swell agents, demulsifiers, VI improvers, pour point depressants, and the like. See, for example, U.S. Pat. No. 5,498,809 for a description of useful lubricating oil composition additives, the disclosure of which is incorporated herein by reference in its entirety.

Examples of dispersants include polyisobutylene succinimides, polyisobutylene succinate esters, Mannich Base ashless dispersants, and the like.

Examples of detergents include metallic and ashless alkyl phenates, metallic and ashless sulfurized alkyl phenates, metallic and ashless alkyl sulfonates, metallic and ashless alkyl salicylates, metallic and ashless saligenin derivatives, and the like.

Examples of antioxidants include alkylated diphenylamines, N-alkylated phenylenediamines, phenyl-α-naphthylamine, alkylated phenyl-α-naphthylamine, dimethyl quinolines, trimethyldihydroquinolines and oligomeric compositions derived therefrom, hindered phenolics, alkylated hydroquinones, hydroxylated thiodiphenyl ethers, alkylidenebisphenols, thiopropionates, metallic dithiocarbamates, 1,3,4-dimercaptothiadiazole and derivatives, oil soluble copper compounds, and the like.

The following are exemplary of such additives and are commercially available from Crompton Corporation: Naugalube® 438, Naugalube 438L, Naugalube 640, Naugalube 635, Naugalube 680, Naugalube AMS, Naugalube APAN, Naugard® PANA, Naugalube TMQ, Naugalube 531, Naugalube 431, Naugard BHT, Naugalube 403, and Naugalube 420, among others.

Examples of anti-wear additives that can be used in combination with the additives of the present invention include organo-borates, organo-phosphites, organo-phosphates, organic sulfur-containing compounds, sulfurized olefins, sulfurized fatty acid derivatives (esters), chlorinated paraffins, zinc dialkyldithiophosphates, zinc diaryldithiophosphates, dialkyldithiophosphate esters, diaryl dithiophosphate esters, phosphosulfurized hydrocarbons, and the like.

The following are exemplary of such additives and are commercially available from The Lubrizol Corporation: Lubrizol 677A, Lubrizol 1095, Lubrizol 1097, Lubrizol 1360, Lubrizol 1395, Lubrizol 5139, and Lubrizol 5604, among others; and from Ciba Corporation: Irgalube 353.

Examples of friction modifiers include fatty acid esters and amides, organo molybdenum compounds, molybdenum dialkyldithiocarbamates, molybdenum dialkyl dithiophosphates, molybdenum disulfide, tri-molybdenum cluster dialkyldithiocarbamates, non-sulfur molybdenum compounds and the like.

The following are exemplary of molybdenum additives and are commercially available from R. T. Vanderbilt Company, Inc.: Molyvan A, Molyvan L, Molyvan 807, Molyvan 856B, Molyvan 822, Molyvan 855, among others. The following are also exemplary of such additives and are commercially available from Asahi Denka Kogyo K.K.: SAKURA-LUBE 100, SAKURA-LUBE 165, SAKURA-LUBE 300, SAKURA-LUBE 31 OG, SAKURA-LUBE 321, SAKURA-LUBE 474, SAKURA-LUBE 600, SAKURA-LUBE 700, among others. The following are also exemplary of such additives and are commercially available from Akzo Nobel Chemicals GmbH: Ketjen-Ox 77M, Ketjen-Ox 77TS, among others, and from Crompton Corporation: Naugalube MolyFM™ 2543.

An example of an anti-foamant is polysiloxane, and the like.

Examples of rust inhibitors are polyoxyalkylene polyol, benzotriazole derivatives, and the like.

Examples of VI improvers include olefin copolymers and dispersant olefin copolymers, and the like.

An example of a pour point depressant is polymethacrylate, and the like.

As noted above, suitable anti-wear compositions may include dihydrocarbyldithiophosphates. Preferably, the hydrocarbyl groups contain an average of at least 3 carbon atoms. Particularly useful are metal salts of at least one dihydrocarbyl dithiophosphoric acid wherein the hydrocarbyl groups contain an average of at least 3 carbon atoms. The acids from which the dihydrocarbyl dithiophosphates can be derived can be illustrated by acids of the formula:

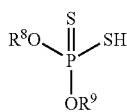

wherein $R^8$ and $R^9$ are the same or different and are alkyl, cycloalkyl, aralkyl, alkaryl, or substituted substantially hydrocarbon radical derivatives of any of the above groups, and wherein the $R^8$ and $R^9$ groups in the acid each have, on average, at least 3 carbon atoms. By "substantially hydrocarbon" is meant radicals containing atoms or groups, e.g., 1 to 4 substituent groups per radical moiety, such as ether, ester, nitro, halogen, or the like, that do not materially affect the hydrocarbon character of the radical.

Specific examples of suitable $R^8$ and $R^9$ radicals include isopropyl, isobutyl, n-butyl, sec-butyl, n-hexyl, heptyl, 2-ethylhexyl, diisobutyl, isooctyl, decyl, dodecyl, tetradecyl, hexadecyl, octadecyl, butylphenyl, o,p-dipentylphenyl, octylphenyl, polyisobutene-(molecular weight about 350)-substituted phenyl, tetrapropylene-substituted phenyl, β-octylbutylnaphthyl, cyclopentyl, cyclohexyl, phenyl, chlorophenyl,o-dichlorophenyl, bromophenyl, naphthenyl, 2-methylcyclohexyl, benzyl, chlorobenzyl, chloropentyl, dichlorophenyl, nitrophenyl, dichlorodecyl, xenyl, and similar radicals. Alkyl radicals having from about 3 to about 30 carbon atoms and aryl radicals having from about 6 to about 30 carbon atoms are preferred. Particularly preferred $R^8$ and $R^9$ radicals are alkyl of from 3 to 12 carbon atoms.

The phosphorodithioic acids are readily obtainable by the reaction of phosphorus pentasulfide and an alcohol or phenol. The reaction involves mixing, at a temperature of about 20° C. to 200° C., 4 moles of the alcohol or phenol with one mole of phosphorus pentasulfide. Hydrogen sulfide is liberated as the reaction takes place. Mixtures of alcohols, phenols, or both can be employed, e.g., mixtures of $C_3$ to $C_{30}$ alcohols, $C_6$ to $C_{30}$ aromatic alcohols, and the like.

The metals useful to make the phosphate salts include Group I metals, Group II metals, aluminum, lead, tin, molybdenum, manganese, cobalt, and nickel. Zinc is the preferred metal. Examples of metal compounds that can be reacted with the acid include lithium oxide, lithium hydroxide, lithium carbonate, lithium pentylate, sodium oxide, sodium hydroxide, sodium carbonate, sodium methylate, sodium propylate, sodium phenoxide, potassium oxide, potassium hydroxide, potassium carbonate, potassium methylate, silver oxide, silver carbonate, magnesium oxide, magnesium hydroxide, magnesium carbonate, magnesium ethylate, magnesium propylate, magnesium phenoxide, calcium oxide, calcium hydroxide, calcium carbonate, calcium methylate, calcium propylate, calcium pentylate, zinc oxide, zinc hydroxide, zinc carbonate, zinc propylate, strontium oxide, strontium hydroxide, cadmium oxide, cadmium hydroxide, cadmium carbonate, cadmium ethylate, barium oxide, barium hydroxide, barium hydrate, barium carbonate, barium ethylate, barium pentylate, aluminum oxide, aluminum propylate, lead oxide, lead hydroxide, lead carbonate, tin oxide, tin butylate, cobalt oxide, cobalt hydroxide, cobalt carbonate, cobalt pentylate, nickel oxide, nickel hydroxide, nickel carbonate, and the like.

In some instances, the incorporation of certain ingredients, particularly carboxylic acids or metal carboxylates, such as, small amounts of the metal acetate or acetic acid, used in conjunction with the metal reactant will facilitate the reaction and result in an improved product. For example, the use of up to about 5% of zinc acetate in combination with the required amount of zinc oxide facilitates the formation of a zinc phosphorodithioate.

The preparation of metal phosphorodithioates is well known in the art and is described in a large number of issued patents, including U.S. Pat. Nos. 3,293,181; 3,397,145; 3,396,109; and 3,442,804; the disclosures of which are hereby incorporated by reference. Also useful as anti-wear additives are amine derivatives of dithiophosphoric acid compounds, such as are described in U.S. Pat. No. 3,637,499, the disclosure of which is hereby incorporated by reference in its entirety.

The zinc salts are most commonly used as anti-wear additives in lubricating oil in amounts of 0.1 to 10, preferably 0.2 to 2, wt. %, based upon the total weight of the lubricating oil composition. They may be prepared in accordance with known techniques by first forming a dithiophosphoric acid, usually by reaction of an alcohol or a phenol with $P_2S_5$ and then neutralizing the dithiophosphoric acid with a suitable zinc compound.

Mixtures of alcohols can be used, including mixtures of primary and secondary alcohols, secondary generally for imparting improved anti-wear properties and primary for thermal stability. In general, any basic or neutral zinc compound could be used, but the oxides, hydroxides, and carbonates are most generally employed. Commercial additives frequently contain an excess of zinc owing to use of an excess of the basic zinc compound in the neutralization reaction.

The zinc dihydrocarbyl dithiophosphates (ZDDP) are oil soluble salts of dihydrocarbyl esters of dithiophosphoric acids and can be represented by the following formula:

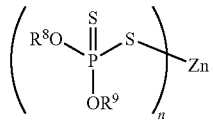

wherein n, $R^8$, and $R^9$ are as described above.

Lubricant Compositions

Compositions, when they contain these additives, are typically blended into a base oil in amounts such that the additives therein are effective to provide their normal attendant functions. Representative effective amounts of such additives are illustrated in TABLE 1.

TABLE 1

| Additives | Preferred Weight % | More Preferred Weight |
|---|---|---|
| V.I. Improver | 1-12 | 1-4 |
| Corrosion Inhibitor | 0.01-3 | 0.01-1.5 |
| Oxidation Inhibitor | 0.01-5 | 0.01-1.5 |
| Dispersant | 0.1-10 | 0.1-5 |
| Lube Oil Flow Improver | 0.01-2 | 0.01-1.5 |
| Detergent/Rust Inhibitor | 0.01-6 | 0.01-3 |
| Pour Point Depressant | 0.01-1.5 | 0.01-0.5 |
| Anti-foaming Agents | 0.001-0.1 | 0.001-0.01 |
| Anti-wear Agents | 0.001-5 | 0.001-1.5 |
| Seal Swell Agents | 0.1-8 | 0.1-4 |
| Friction Modifiers | 0.01-3 | 0.01-1.5 |
| Lubricating Base Oil | Balance | Balance |

When other additives are employed, it may be desirable, although not necessary, to prepare additive concentrates comprising concentrated solutions or dispersions of the subject additives of this invention together with one or more of said other additives (said concentrate when constituting an additive mixture being referred to herein as an additive-package) whereby several additives can be added simultaneously to the base oil to form the lubricating oil composition. Dissolution of the additive concentrate into the lubricating oil can be facilitated by solvents and by mixing accompanied by mild heating, but this is not essential. The concentrate or additive-package will typically be formulated to contain the additives in proper amounts to provide the desired concentration in the final formulation when the additive-package is combined with a predetermined amount of base lubricant. Thus, the subject additives of the present invention can be added to small amounts of base oil or other compatible solvents along with other desirable additives to form additive-packages containing active ingredients in collective amounts of, typically, from about 2.5 to about 90 percent, preferably from about 15 to about 75 percent, and more preferably from about 25 percent to about 60 percent by weight additives in the appropriate proportions with the remainder being base oil. The final formulations can typically employ about 1 to 20 weight percent of the additive-package with the remainder being base oil.

All of the weight percentages expressed herein (unless otherwise indicated) are based on the active ingredient (AI) content of the additive, and/or upon the total weight of any additive-package, or formulation, which will be the sum of the AI weight of each additive plus the weight of total oil or diluent.

In general, the lubricant compositions of the invention contain the additives in a concentration ranging from about 0.05 to about 30 weight percent. A concentration range for the additives ranging from about 0.1 to about 10 weight percent based on the total weight of the oil composition is preferred. A more preferred concentration range is from about 0.2 to about 5 weight percent. Oil concentrates of the additives can contain from about 1 to about 75 weight percent of the additive reaction product in a carrier or diluent oil of lubricating oil viscosity.

In general, the additives of the present invention are useful in a variety of lubricating oil base stocks. The lubricating oil base stock is any natural or synthetic lubricating oil base stock fraction having a kinematic viscosity at 100° C. of about 2 to about 200 cSt, more preferably about 3 to about 150 cSt, and most preferably about 3 to about 100 cSt. The lubricating oil base stock can be derived from natural lubricating oils, synthetic lubricating oils or mixtures thereof. Suitable lubricating oil base stocks include base stocks obtained by isomerization of synthetic wax and wax, as well as hydrocracked base stocks produced by hydrocracking (rather than solvent extracting) the aromatic and polar components of the crude. Natural lubricating oils include animal oils, such as lard oil, vegetable oils (e.g., canola oils, castor oils, sunflower oils), petroleum oils, mineral oils, and oils derived from coal or shale.

Synthetic oils include hydrocarbon oils and halo-substituted hydrocarbon oils, such as polymerized and interpolymerized olefins, gas-to-liquids prepared by Fischer-Tropsch technology, alkylbenzenes, polyphenyls, alkylated diphenyl ethers, alkylated diphenyl sulfides, as well as their derivatives, analogs, homologs, and the like. Synthetic lubricating oils also include alkylene oxide polymers, interpolymers, copolymers, and derivatives thereof, wherein the terminal hydroxyl groups have been modified by esterification, etherification, etc.

Another suitable class of synthetic lubricating oils comprises the esters of dicarboxylic acids -with a variety of alcohols. Esters useful as synthetic oils also include those made from $C_5$ to $C_{12}$ monocarboxylic acids and polyols and polyol ethers. Other esters useful as synthetic oils include those made from copolymers of a-olefins and dicarboxylic acids that are esterified with short or medium chain length alcohols. The following are exemplary of such additives and are commercially available from Akzo Nobel Chemicals SpA: Ketjenlubes 115, 135, 165, 1300, 2300, 2700, 305, 445, 502, 522, and 6300, among others.

Silicon-based oils, such as the polyalkyl-, polyaryl-, polyalkoxy-, or polyaryloxy-siloxane oils and silicate oils, comprise another useful class of synthetic lubricating oils. Other synthetic lubricating oils include liquid esters of phosphorus-containing acids, polymeric tetrahydrofurans, poly α-olefins, and the like.

The lubricating oil may be derived from unrefined, refined, re-refined oils, or mixtures thereof. Unrefined oils are obtained directly from a natural source or synthetic source (e.g., coal, shale, or tar and bitumen) without further purification or treatment. Examples of unrefined oils include a shale oil obtained directly from a retorting operation, a petroleum oil obtained directly from distillation, or an ester oil obtained directly from an esterification process, each of which is then used without further treatment. Refined oils are similar to unrefined oils, except that refined oils have been treated in one or more purification steps to improve one or more properties. Suitable purification techniques include distillation, hydrotreating, dewaxing, solvent extraction, acid or base extraction, filtration, percolation, and the like, all of which are well-known to those skilled in the art. Re-refined oils are obtained by treating refined oils in processes similar to those used to obtain the refined oils. These re-refined oils are also known as reclaimed or reprocessed oils and often are additionally processed by techniques for removal of spent additives and oil breakdown products.

Lubricating oil base stocks derived from the hydroisomerization of wax may also be used, either alone or in combination with the aforesaid natural and/or synthetic base stocks. Such wax isomerate oil is produced by the hydroisomerization of natural or synthetic waxes or mixtures thereof over a hydroisomerization catalyst. Natural waxes are typically the slack waxes recovered by the solvent dewaxing of mineral oils; synthetic waxes are typically the wax produced by the Fischer-Tropsch process. The resulting isomerate product is typically subjected to solvent dewaxing and fractionation to recover various fractions having a specific viscosity range. Wax isomerate is also characterized by possessing very high viscosity indices, generally having a VI of at least 130, preferably at least 135 or higher and, following dewaxing, a pour point of about −20° C. or lower.

The additives of the present invention are especially useful as components in many different lubricating oil compositions. The additives can be included in a variety of oils with lubricating viscosity, including natural and synthetic lubricating oils and mixtures thereof. The additives can be included in crankcase lubricating oils for spark-ignited and compression-ignited internal combustion engines. The compositions can also be used in gas engine lubricants, turbine lubricants, automatic transmission fluids, gear lubricants, compressor lubricants, metal-working lubricants, hydraulic fluids, and other lubricating oil and grease compositions. The additives can also be used in motor fuel compositions.

The advantages and the important features of the present invention will be more apparent from the following examples.

EXAMPLES

The following examples demonstrate the efficacy of the substituted 1,3-dithiolane-2-thiones as lubricant additives, alone and in synergistic combination with phosphorus-containing additives, such as zinc dialkyldithiophosphate. In addition, they show no harm in corrosion testing.

Example 1

Hexahydro-1-3-benzodithiole-2-thione

A 250 mL 3-neck flask was charged with 2.96 grams of sodium hydroxide and 6 mL of water. 1-Butanol, 80 mL, was added, followed by 8.9 mL of carbon disulfide. The mixture was stirred, then 7.50 mL of cyclohexene oxide was added, and a mild exotherm was noted. The mixture was stirred with heating at 35-45° C. for 90 minutes, and then heated to 70° C. and stirred for 3 hours. The mixture was allowed to stand at room temperature overnight. The product was recovered by filtration, washed with water, then air and oven dried to yield 11.9 grams of fine bright yellow crystals.

Example 2

4-Octyl-1,3-dithiolane-2-thione

A 100 mL 4-neck flask (equipped with an overhead stirrer, a spiral condenser vented to a caustic scrubber, and a Claisen head with a thermocouple and a nitrogen inlet) was charged with 4.4 grams of 50% sodium hydroxide and 46 grams of 1-butanol. Carbon disulfide, 4.2 grams, was added, followed by 8.6 grams of 1,2-epoxydecane. The reaction was stirred for one hour at 50° C., and then 20 mL of water was added. The organic phase was taken up in xylenes, and extracted twice with water, then dried over sodium sulfate. The mixture was filtered, and volatiles were removed by rotary evaporation to yield 9.5 grams of a yellow oil.

Example 3

4-Decyl-1,3-dithiolane-2-thione

A 100 mL 3-neck flask was charged with 4.45 grams of sodium hydroxide and 4.60 grams of water. Once the sodium hydroxide was dissolved, 50 mL of I-butanol was added. Carbon disulfide, 6.8 mL, was added over 20 minutes (26-32° C.), followed by 11.3 mL of 1,2-epoxydodecane, keeping the temperature below 33° C. The mixture was then heated to 50° C. for 2.6 hours, then stirred at 70° C. for three hours. The reaction was cooled to 20° C. and then 10 mL of water was added in two parts. The reaction was taken up in xylenes and water. The aqueous layer was removed, and the organics extracted three times with water. Volatiles were removed by rotary evaporation to yield 12.61 grams of a clear yellow oil.

Example 4

4-Dodecyl-1,3-dithiolane-2-thione

A 250 mL 3-neck flask was charged with 3.54 grams of sodium hydroxide and 6 mL of water. 1-Butanol, 80 mL, was added, followed by 4.8 mL of carbon disulfide. The mixture was stirred, then 7.50 mL of 1,2-epoxytetradecane (85% technical grade) was added. The mixture was stirred with heating at 50° C. for 30 minutes, and then heated to 70° C. and stirred for 1 hour. The reaction mixture was taken up in xylenes, and washed twice with water. The reaction mixture was filtered through diatomaceous earth, and volatiles were removed by rotary evaporation to yield 19.5 grams of a mixture of yellow crystals with some yellow oil.

Example 5

4-Tetradecyl-1,3-dithiolane-2-thione

A 100 mL 4-neck flask (equipped with an overhead stirrer, a spiral condenser vented to a caustic scrubber, and a Claisen head with a thermocouple and a nitrogen inlet) was charged with 2.53 grams of sodium hydroxide and 4.5 mL of water. Once the caustic was dissolved, 40 mL of 1-butanol was added. Carbon disulfide, 7.6 mL, was added, followed by 13.7 grams of 1,2-epoxyhexadecane (85%) in four portions. The reaction was stirred for two hours at 50° C., and then three hours at 70° C. The reaction was allowed to cool to 35° C., and 3.6 mL of glacial acetic acid was added. The reaction mass was warmed slightly, and 10 mL of water was added. The mixture was taken up in about 100 mL of xylenes, and the aqueous layer was removed. The organics were extracted three times with 100 mL portions of water. Volatiles were removed by rotary evaporation to yield 17.98 grams of a yellow oil.

Examples 6-7

1,3-Dithiolane-2-thione Derivative of Epoxidized 2-Ethylhexyl Tallate

A 1000 mL 4-neck flask was charged with 22.2 grams of sodium hydroxide and 38 grams of water. The material was stirred, and then 428.5 grams of I-butanol was added, and the mixture was stirred for 15 minutes. Carbon disulfide, 38.1 grams, was added at 26° C. over 30 minutes. The mixture was stirred for 30 minutes more, and then 170.2 grams of Drapex® 4.4 epoxidized 2-ethylhexyl tallate was added dropwise over 45 minutes. The reaction mixture was stirred at 50° C. for two hours, and then at 70° C. for three hours. The reaction mixture was cooled to room temperature, and brought to pH 8 by addition of acetic acid. Water was added (100 mL), and the mixture was stirred for 15 minutes. The reaction mass was transferred to a separatory funnel and the aqueous phase was removed. Xylenes (450 mL) were added, and the product was washed twice with 200 mL portions of water. The product was dried over sodium sulfate and magnesium sulfate and then filtered. Volatiles were removed by rotary evaporation to give 186.6 grams of a clear yellow liquid.

Examples 8-9

1,3-Dithiolane-2-thione Derivative of Epoxidized 2-Ethylhexyl Tallate

A 1000 mL 4-neck flask (equipped with an overhead stirrer, a condenser vented to a caustic scrubber, an addition runnel, and a thermocouple/nitrogen inlet) was charged with 21.0 grams of sodium hydroxide and 40 grams of water. The material was stirred, and then 431 grams of 1-butanol was added and the mixture was stirred for five minutes. Carbon disulfide, 83.04 grams, was added at 29-32° C. over 50 minutes. The mixture was stirred for 15 minutes more, and then 168.8 grams of Drapex 4.4 epoxidized 2-ethylhexyl tallate (Crompton Corp.) was added dropwise over 24 minutes. The reaction mixture was heated to 50° C., and stirred at 50° C. for two hours. The temperature was increased to 70° C., and the reaction was stirred for an additional three hours. The reaction mixture was cooled to 65° C. and 30 mL of glacial acetic acid was added. Water was added (100 mL). The mixture was stirred for 40 minutes. The reaction mass was transferred to a separatory funnel and the aqueous phase was removed. Xylenes (450 mL) were added, and the product was washed four times with 100 mL portions of water. The product was dried over magnesium sulfate, and then filtered through a Büchner funnel with Whatman #4 paper, and then through diatomaceous earth. Volatiles and solvent were removed by rotary evaporation to give a clear yellow liquid.

Anti-Wear Four-Ball Testing

The anti-wear properties of the 1,3-dithiolane-2-thiones in a fully formulated American Petroleum Institute (API) Group II lubricating oil were determined in the Four-Ball Wear Test under the ASTM D 4172 test conditions. The testing for these examples was done on a Falex Variable Drive Four-Ball Wear Test Machine. Four balls are arranged in an equilateral tetrahedron. The lower three balls are clamped securely in a test cup filled with lubricant and the upper ball is held by a chuck that is motor-driven. The upper ball rotates against the fixed lower balls. Load is applied in an upward direction through a weight/lever arm system. Loading is through a continuously variable pneumatic loading system. Heaters allow operation at elevated oil temperatures. The three stationary steel balls are immersed in 10 milliliters of sample to be tested, and the fourth steel ball is rotated on top of the three stationary balls in "point-to-point contact." The machine is operated for one hour at 75° C. with a load of 40 kilograms and a rotational speed of 1,200 revolutions per minute. The fully formulated lubricating oil contained all the additives typically found in a motor oil (with different anti-wear agents as noted in TABLE 2) as well as 0.5 wt.% cumene hydroperoxide to help simulate the environment within a running engine.

The additives were tested for effectiveness in a motor oil formulation and compared to identical formulations with and without any zinc dialkyldithiophosphate. It will be apparent from examination of the data that the use of these hydroxy ester additives in combination with phosphorus-containing additives offers synergistic improvement in performance over either type of additive alone.

Anti-Wear Cameron-Plint TE77 High Frequency Friction Machine Testing

The anti-wear properties of the additives of this invention in a fully formulated API Group II lubricating oil were determined in the Cameron-Plint TE77 High Frequency Friction Machine Test. The specimen parts (6 mm diameter AISI 52100 steel ball of 800±20 kg/mm$^2$ hardness and hardened ground NSOH B01 gauge plate of RC 60/0.4 micron) were rinsed and then sonicated for 15 minutes with technical grade hexanes. This procedure was repeated with isopropyl alcohol. The specimens were dried with nitrogen and set into the TE77. The oil bath was filled with 10 mL of sample. The test was run at a 30 Hertz frequency, 100 Newton load, 2.35 mm amplitude. The test starts with the specimens and oil at room temperature. Immediately, the temperature was ramped over 15 minutes to 50° C., where it dwelled for 15 minutes. The temperature was then ramped over 15 minutes to 1 00° C., where it dwelled for 45 minutes. A third temperature ramp over 15 minutes to 150° C. was followed by a final dwell at 150° C. for 15 minutes. The total length of the test was 2 hours. At the end of test, the wear scar diameter on the 6 mm ball was measured using a Leica StereoZoom6® Stereomicroscope and a Mitutoyo 164 series Digimatic Head. The fully formulated lubricating oils tested contained 1 weight % cumene hydroperoxide to help simulate the environment within a running engine.

The additives were tested for effectiveness in motor oil formulations and compared to identical formulations with and without any zinc dialkyldithiophosphate. In TABLE 2 the numerical value of the test results (Wear Scar Diameter, mm) decreases with an increase in effectiveness.

Also determined was the maximum depth of the wear scar on the plate. This is measured using a profilimeter (mm). The number in parentheses (#x), is the number of repeat experiments used for the average value.

TABLE 2

Anti-Wear Test Data

| Example | Anti-Wear Chemical Name | Four-Ball | | Cameron Plint | | |
|---------|-------------------------|-----------|-----------|---------------|---|---|
| | | Ave. of Scar (mm) | No. of Repititions | Ave. Ball Scars (mm) | Ave. Plate Scars Depth (μm) | No. of Repetitions |
| A | ZDDP 1% (Comparative) | 0.481 | 49 | 0.424 | 1.79 | 43 |
| B | No Anti-wear (Comparative) | 0.794 | 40 | 0.754 | 15.54 | 52 |
| 1 | Hexahydro-1-3-benzodithiole-2-thione | 0.497 | 2 | 0.415 | 8.42 | 2 |
| 2 | 4-Octyl-1,3-dithiolane-2-thione | 0.587 | 2 | — | — | — |
| 3 | 4-Decyl-1,3-dithiolane-2-thione | 0.420 | 2 | — | — | — |
| 4 | 4-Dodecyl-1,3-dithiolane-2-thione | 0.456 | 2 | 0.801 | 12.74 | 2 |
| 5 | 4-Tetradecyl-1,3-dithiolane-2-thione | 0.427 | 2 | — | — | — |
| 6 | 1,3-Dithiolane-2-thione derivative of epoxidized 2-ethylhexyl tallate | 0.440 | 11 | 0.785 | 11.669 | 2 |
| 7 | 1,3-Dithiolane-2-thione derivative of epoxidized 2-ethylhexyl tallate) 0.50% ZDDP 0.50% | 0.385 | 2 | 0.361 | 2.129 | 2 |
| 8 | 1,3-Dithiolane-2-thione derivative of epoxidized 2-ethylhexyl tallate | 0.475 | 2 | 0.740 | 7.975 | 2 |
| 9 | 1,3-Dithiolane-2-thione derivative of epoxidized 2-ethylhexyl tallate) 0.50% ZDDP 0.50% | 0.405 | 2 | 0.448 | 2.115 | 2 |

Lead and Copper Corrosion Testing

In TABLE 3 are the results of a Cummins bench test for measuring the degree of Cu and Pb corrosion of an oil formulation. The Cummins bench test is part of the API CH-4 category for diesel engine oils. Four metal coupons (25.4 mm squares) of pure lead, copper, tin, and phosphor-bronze are immersed in 100 mL of oil at 121° C. with air bubbling through (5 L/hr) for 168 hours. The used oil is analyzed for metals and the copper sample is examined for discoloration. The limits for API CH-4 are 20 ppm Cu, 120 ppm Pb, 50 ppm Sn in used oil and 3 max for the ASTM D 130 rating of the copper square. Additives were blended into a fully formulated SAE 15-W40 oil with ILSAC GF-2 credentials. In the first row of TABLE 3 are data generated on the SAE 15W-40 oil without any top treat of other additives. The substituted 1,3-dithiolane-2-thione did very well on Pb corrosion with passing results.

TABLE 3

ASTM D 5968 Corrosion Bench Test of Engine Oil at 121° C.

| Additive (in Rotella T SAE 15W-40) | Weight % Additive | Copper (ppm) | Lead (ppm) | ASTM D130 |
|---|---|---|---|---|
| Reference | 0.0 | 7 | 11.9 | 1b |
| 1,3-Dithiolane-2-thione derivative of epoxidized 2-ethylhexyl tallate | 1.0 | 9.5 | 3.0 | 1b |
| 1,3-Dithiolane-2-thione derivative of epoxidized 2-ethylhexyl tallate | 1.0 | 7 | 3.3 | 1b |

In view of the many changes and modifications that can be made without departing from principles underlying the invention, reference should be made to the appended claims for an understanding of the scope of the protection to be afforded the invention.

What is claimed is:

1. A composition comprising:
   (A) a lubricant or a hydrocarbon fuel, and
   (B) at least one 1,3-dithiolane-2-thione of formula (I):

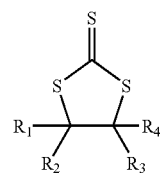

(I)

wherein:
   $R_1$ is a carboxy alkyl of the structure: $(CH_2)_p CO_2 R_5$
   wherein:
      p is from 1 to 50, and
      $R_5$ is selected from the group consisting of hydrocarbyl, chain-substituted saturated hydrocarbyl, and chain-substituted unsaturated hydrocarbyl;
   $R_2$, $R_3$, and $R_4$ are independently selected from the group consisting of hydrogen, alkyl, and alkenyl;
   wherein said alkyl and alkenyl groups are unsubstituted or substituted with OH, SH, oxirane, thiirane, or 1,3-dithiolane-2-thione.

2. The composition of claim 1 wherein the 1,3-dithiolane-2-thione is prepared by The reaction of an alkali metal xanthate with an epoxidized olefin of from 8 to 36 carbons.

3. The composition of claim 2 wherein the epoxidized olefin is an α-olefin.

4. The composition of claim 2 wherein the epoxidized olefin is an epoxidized tallate ester.

5. The composition of claim 1 further comprising at least one phosphorus-containing additive.

6. The composition of claim 5 wherein at least one phosphorus-containing additive is a dihydrocarbyldithiophosphate.

7. The composition of claim 1 wherein the 1,3-dithiolane-2-thione is selected from the group consisting of hexahydro-1-3-benzodithiole-2-thione, 4-octyl-1,3-dithiolane-2-thione, 4-decyl-1,3-dithiolane-2-thione, 4-dodecyl-1,3-dithiolane-2-thione, 4-tetradecyl-1,3-dithiolane-2-thione, and a 1,3-dithiolane-2-thione derivative of epoxidized 2-ethylhexyl tallate.

8. The 1,3-dithiolane-2-thione derivative of epoxidized 2-ethylhexyl tallate.

9. A method for improving the anti-corrosion, anti-fatigue, anti-wear, and extreme pressure properties of lubricants and hydrocarbon fuels comprising adding to said lubricants and hydrocarbon fuels a functional property-improving amount of at least one 1,3-dithiolane-2-thione of formula (I):

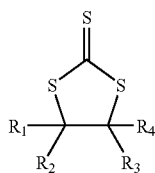

(I)

wherein:
R$_1$ is a carboxy alkyl of the structure: $(CH_2)_p CO_2 R_5$
wherein:
p is from 1 to 50, and
R$_5$ is selected from the group consisting of hydrocarbyl, chain-substituted saturated hydrocarbyl, and chain-substituted unsaturated hydrocarbyl;
R$_2$, R$_3$, and R$_4$ are independently selected from the group consisting of hydrogen, alkyl, and alkenyl;
wherein said alkyl and alkenyl groups are unsubstituted or substituted with OH, SH, oxirane, thiirane, or 1,3-dithiolane-2-thione.

10. The method of claim 9 wherein a phosphorus-containing additive is also added to The lubricants and hydrocarbon fuels.

11. The method of claim 10 wherein the phosphorus-containing additive is a dihydrocarbyldithiophosphate.

12. The method of claim 9 wherein the 1,3-dithiolane-2-thione is selected from the group consisting of hexahydro-1-3-benzodithiole-2-thione, 4-octyl-1,3-dithiolane-2-thione, 4-decyl-1,3-dithiolane-2-thione, 4-dodecyl-1,3-dithiolane-2-thione, 4-tetradecyl-1,3-dithiolane-2 -thione, and a 1,3-dithiolane-2-thione derivative of epoxidized 2-ethylhexyl tallate.

13. A method for producing a 1,3-dithiolane-2-thione of formula (I):

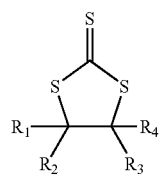

(I)

wherein:
R$_1$ is selected from the group consisting of hydrogen, alkyl, alkoxy, and carboxy alkyl of the structure: $(CH_2)_p CO_2 R_5$
wherein:
p is from 1 to 50;
R$_5$ is selected from the group consisting of hydrocarbyl, chain-substituted saturated hydrocarbyl, and chain-substituted unsaturated hydrocarbyl;
R$_2$, R$_3$, and R$_4$ are independently selected from the group consisting of hydrogen, alkyl, and alkenyl;
wherein said alkyl and alkenyl groups are unsubstituted or substituted with OH, SH, oxirane, thiirane, or 1,3-dithiolane-2-thione; or
R$_1$ and R$_3$ are fused together to form a ring of from 3 to 10 carbon atoms, which can be further substituted with alkyl, cycloalkyl, alkenyl, aryl or alkoxy groups, and can contain ether or ester functionalities, the method comprising:
reacting a sodium xanthate with an epoxidized 2-ethylhexyl tallate.

* * * * *